(12) United States Patent
Worth et al.

(10) Patent No.: US 10,195,177 B2
(45) Date of Patent: Feb. 5, 2019

(54) USE OF ACYL-HOMOSERINE LACTONE DERIVATIVES AS ANTI-THROMBOTIC AGENTS

(71) Applicant: The University of Toledo, Toledo, OH (US)

(72) Inventors: Randall G. Worth, Toledo, OH (US); Glenn R. Westphal, Toledo, OH (US); Brenton R. Keeley, Toledo, OH (US); Leah M. Wuescher, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/764,684

(22) PCT Filed: Sep. 27, 2016

(86) PCT No.: PCT/US2016/053905
§ 371 (c)(1),
(2) Date: Mar. 29, 2018

(87) PCT Pub. No.: WO2017/058757
PCT Pub. Date: Apr. 6, 2017

(65) Prior Publication Data
US 2018/0280345 A1 Oct. 4, 2018

Related U.S. Application Data

(60) Provisional application No. 62/236,086, filed on Oct. 1, 2015.

(51) Int. Cl.
*A61K 31/365* (2006.01)
*A61K 45/06* (2006.01)

(52) U.S. Cl.
CPC ............ *A61K 31/365* (2013.01); *A61K 45/06* (2013.01)

(58) Field of Classification Search
CPC .................................................. A61K 31/365
IPC ...................................... A61K 31/365,31/3425
See application file for complete search history.

(56) References Cited

U.S. PATENT DOCUMENTS

| 5,776,974 | A | * | 7/1998 | Bycroft | ............... | A61K 31/365 |
| | | | | | | 514/445 |
| 5,969,158 | A | | 10/1999 | Bycroft et al. | | |
| 6,602,905 | B1 | * | 8/2003 | Gardiner | ............. | A61K 31/365 |
| | | | | | | 514/472 |
| 7,498,292 | B2 | | 3/2009 | Suga et al. | | |
| 8,049,020 | B2 | | 11/2011 | Pritchard et al. | | |
| 2003/0148945 | A1 | | 8/2003 | McNicol et al. | | |
| 2007/0010477 | A1 | * | 1/2007 | Dolnick | ............... | A61K 31/337 |
| | | | | | | 514/49 |

FOREIGN PATENT DOCUMENTS

WO 2014153415 A2 9/2014

OTHER PUBLICATIONS

International Search Report and Written Opinion, Application No. PCT/US16/53905, dated Dec. 20, 2016.
Khajanchi, et al., "Immunomodulatory and Protective Roles of Quorum-Sensing Signaling Molecules N-Acyl Homoserine Lactones during Infection of Mice with Aeromonas hydrophila", Infection and Immunity, Jul. 2011, pp. 2646-2657.

* cited by examiner

*Primary Examiner* — Theodore R. West
*Assistant Examiner* — George W Kosturko
(74) *Attorney, Agent, or Firm* — MacMillan, Sobanski & Todd, LLC (57) ABSTRACT

Uses of acyl-homoserine lactone compounds are described. In particular, uses of acyl-homoserine lactone compounds as anti-thrombotic agents, to inhibit platelets from becoming hypersensitive, and/or to prevent thrombosis, are described.

10 Claims, 6 Drawing Sheets

USE OF ACYL-HOMOSERINE LACTONE DERIVATIVES AS ANTI-THROMBOTIC AGENTS

RELATED APPLICATIONS

This application claims priority to U.S. Provisional Application Ser. No. 62/236,086 filed under 35 U.S.C. § 111(b) on Oct. 1, 2015, the disclosure of which is incorporated herein by reference in its entirety.

STATEMENT REGARDING FEDERALLY SPONSORED RESEARCH

This invention was made with government support under Grant Number RO1 HL 122401 awarded by National Institutes of Health. The government has certain rights in this invention.

BACKGROUND OF THE INVENTION

Various ailments cause a person to become more likely to suffer a thrombotic event. For example, systemic lupus erythematosus (referred to SLE or lupus), rheumatoid arthritis (RA), and certain cancers are known to be pro-thrombotic conditions. Current therapies for treating pro-thrombotic platelets include molecules that can be divided into families based on their mechanism of action: cyclooxygenase inhibitors (aspirin, triflusal), adenosine diphosphate receptor inhibitors (clopidogrel, prasugrel, ticagrelor, ticlopidine), phosphodiesterase inhibitors (cilostazol), protease-activated receptor antagonists (vorapaxar), glycoprotein IIB/IIIA inhibitors (abciximab, eptifibatide, tirofiban), and adenosine reuptake inhibitors (dipyridamole). Anticoagulants are emerging as a favored mode of treatment for thrombosis. These drugs are all beneficial to patients who are thrombotic. However, the downfall of these drugs is that some patients develop severe bleeding tendancies because these drugs inhibit essential pathways responsible for maintaining vascular hemostasis. Furthermore, some patients are non-responders to these drugs. Therefore, there is a need in the art for new and improved treatments for pro-thrombotic conditions.

SUMMARY OF THE INVENTION

Provided herein is a method of inhibiting platelets from becoming hypersensitive, the method involving administering an effective amount of an acyl-homoserine lactone compound to a patient in need thereof, and inhibiting platelets in the patient from becoming hypersensitive, where the acyl-homoserine lactone compound has the general formula of Formula I:

Formula I where $R_1$ is hydrogen, a carbonyl, or $CH_3$, and $R_2$ is either hydrogen or $(CH_2)_nCH_3$, where n ranges from 0 to 15. In certain embodiments, $R_1$ is a carbonyl, $R_2$ is $(CH_2)_nCH_3$, and n is 2, 4, 6, 8, or 10.

In particular embodiments, the acyl-homoserine lactone compound consists essentially of 12C-AHL, having Formula II:

Formula II

In particular embodiments, the acyl-homoserine lactone compound consists essentially of 10C-AHL, having Formula III:

Formula III

In particular embodiments, the acyl-homoserine lactone compound consists essentially of 8C-AHL, having Formula IV:

Formula IV

In particular embodiments, the acyl-homoserine lactone compound consists essentially of 6C-AHL, having Formula V:

Formula V

In particular embodiments, the acyl-homoserine lactone compound consists essentially of 14C-AHL, having Formula VI:

Formula VI

In certain embodiments, the patient exhibits normal hemostasis following administration of the acyl-homoserine lactone compound.

In certain embodiments, the acyl-homoserine lactone compound is administered at a desired concentration, and the acyl-homoserine lactone compound inhibits aggIgG-mediated platelet activation. For example, the acyl-homoserine lactone compound can be administered at a concentration of about 20 μM or less. In certain embodiments, the acyl-homoserine lactone compound is administered at a concentration of about 200 μM or less, and the acyl-homoserine lactone compound inhibits thrombin-induced platelet activation.

In certain embodiments, the acyl-homoserine lactone compound inhibits signaling activities in the platelets. In certain embodiments, the patient has a pro-thrombotic condition. In certain embodiments, the patient has lupus. In certain embodiments, the patient has rheumatoid arthritis. In certain embodiments, the patient has cancer. In certain embodiments, the patient has autoimmune diseases. In certain embodiments, the patient has infectious diseases. In certain embodiments, the patient has inflammatory diseases. In certain embodiments, the patient has metabolic diseases.

In certain embodiments, the acyl-homoserine lactone compound is co-administered with at least one chemotherapeutic agent, lupus treatment, or rheumatoid arthritis treatment. In particular embodiments, the chemotherapeutic agent, lupus treatment, or rheumatoid arthritis treatment is selected from the group consisting of: platinum coordination compounds; taxane compounds; topoisomerase I inhibitors; topoisomerase II inhibitors; anti-tumor vinca alkaloids; anti-tumor nucleoside derivatives; alkylating agents; anti-tumor anthracycline derivatives; HER2 antibodies; estrogen receptor antagonists or selective estrogen receptor modulators; aromatase inhibitors; differentiating agents; DNA methyl transferase inhibitors; kinase inhibitors; farnesyltransferase inhibitors; HDAC inhibitors; other inhibitors of the ubiquitin-proteasome pathway; PI3 kinase inhibitors; corticosteroids; anti-inflammatory agents; immunosuppressants; anti-malarial drugs; statins; diuretics; disease-modifying antirheumatic drugs (DMARDs); anti-inflammatory agents; corticosteroids; and proteins.

Further provided is a pharmaceutical composition comprising an acyl-homoserine lactone compound, at least one chemotherapeutic agent, lupus treatment, or rheumatoid arthritis treatment, and a pharmaceutically acceptable excipient, diluent, or carrier, where the acyl-homoserine lactone compound has Formula I:

Formula I where $R_1$ is hydrogen, a carbonyl, or $CH_3$, and $R_2$ is either hydrogen or $(CH_2)_nCH_3$, where n ranges from 0 to 15. In certain embodiments, the acyl-homoserine lactone compound comprises 10C-AHL or 12C-AHL.

Also provided is a kit comprising a first container housing an acyl homoserine lactone compound, and a second container housing at least one of a chemotherapeutic agent, a lupus treatment, or a rheumatoid arthritis treatment, where the acyl-homoserine lactone compound has Formula I:

Formula I where $R_1$ is hydrogen, a carbonyl, or $CH_3$, and $R_2$ is either hydrogen or $(CH_2)_nCH_3$, where n ranges from 0 to 15. In certain embodiments, the acyl-homoserine lactone compound comprises 10C-AHL or 12C-AHL.

BRIEF DESCRIPTION OF THE DRAWINGS

FIGS. 2A-2B: Effect of AHLs on aggIgG induced platelet hypersensitivity to thrombin. Human platelets were incubated with PBS or aggIgG for 15 minutes then stimulated by several doses of thrombin, and surface expression of CD62P was measured by flow cytometry. (FIG. 2A.) Human platelets were incubated with 20 μM AHLs with modified acyl chains then incubated with aggIgG followed by thrombin, and plasma membrane CD62P was measured by flow cytometry. (FIG. 2B.) The effective concentration of thrombin that resulted in a 50% maximal CD62P expression (EC50) was calculated and plotted.

FIGS. 3A-3C: Effect of AHLs on tyrosine phosphorylation. Human platelets were incubated with PBS or 12C-AHL then left unstimulated or stimulated with 500 mg/ml aggIgG or 0.1 U/ml thrombin. Whole cell lysates were prepared as described in the examples and blotted for anti-phosphotyrosine or anti-GAPDH as loading control. (FIG. 3A.) To determine band intensities, total band intensity in the phosphorylation gel was divided by the GAPDH signal and plotted as total band intensity. (FIG. 3B.) Intensity of the indicated band was compared to GAPDH and plotted as band intensity. (FIG. 3C.)

FIGS. 4A-4C: Effect of AHLs on platelet-mediated phagocytosis. Human platelets were incubated as indicated in the examples and analyzed by flow cytometry for FITC-IgG and PE-anti-IgG. (FIG. 4A.) Platelets were incubated with PBS, 10C- or 12C-AHLs or cytochalasin D (positive control to block phagocytosis), then exposed to FITC-IgG-coated 1.5 mm beads for 30 minutes, labeled with anti-IgG conjugated to PE and analyzed by flow cytometry for FITC-IgG and PE-anti-IgG. (FIG. 4B.) Platelets were treated as in FIG. 4B and surface CD62P expression was measured by flow cytometry. *p<0.01, **p<0.005. (FIG. 4C.)

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art.

It will be appreciated by one of ordinary skill in the art that asymmetric centers may exist in any of the compounds described herein. Thus, the compounds and pharmaceutical compositions thereof may be in the form of an individual enantiomer, diastereomer, or geometric isomer, or may be in the form of a mixture of stereoisomers. In certain embodiments, the compounds herein are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

Any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds. Combinations of substituents and variables envisioned are preferably those that result in the formation of stable compounds useful in the treatment of pro-thrombotic conditions and/or the prevention of thrombosis.

General Description

Patients with several diseases, such as lupus, rheumatoid arthritis, and certain cancers, are more prone to thrombosis than the general population. The mechanisms behind this increased thrombosis are not completely understood, but pathways leading to platelets becoming pro-thrombotic have been identified. In accordance with the present disclosure, a family of small molecules prevents platelets from becoming pro-thrombotic. Importantly, these small molecules prevent the transition to a pro-thrombotic state without impacting normal hemostatic responses. As described in the examples, it has been observed that treating platelets with these small molecules inhibits hypersensitivity of platelets treated with immune complexes like those from patients with systemic lupus erythrematosus, while not interfering with traditional thrombotic agonists. These molecules have significant clinical benefit to patients with autoimmune disease, malignancies, and many other ailments which lead to increased thrombosis. Advantageously, these small molecules maintain the ability of platelets to respond to thrombotic agents (thombin, collagen, fibrinogen, ADP) while inhibiting the ability of platelets to become hypersensitive to such thrombotic agents. This can save lives by decreasing the severity of thrombosis in patients, and thereby preventing strokes and heart attacks, but still allowing for normal coagulation, and thereby preventing bleeding disorders. Whereas current therapies for thrombotic conditions target major pathways involved in platelet activation, the small molecules described herein target a minor pathway only involved in hypersensitivity but not in coagulation.

The small molecules useful for inhibiting platelets from becoming hypersensitive have the following general Formula I:

Formula I where $R_1$ is hydrogen, a carbonyl, or $CH_3$, and $R_2$ is either hydrogen or $(CH_2)_nCH_3$, where n ranges from 0 to 15. These small molecules are known as acyl-homoserine lactones (AHLs). It is understood that the use of either the L- or D-enantiomer, as well as racemic mixtures, of any AHL compound is possible.

While many AHL derivatives are encompassed within the present disclosure, specifically included are 10C-AHL and 12C-AHL. 12C-AHL is also known as N-oxo-dodecanoyl-L-homoserine lactone, 3-oxo-N-(tetrahydro-2-oxo-3-furanyl)dodecanamide, or 3-oxo-N-(2-oxotetrahydrofuran-3-yl) dodecanamide, and has the following Formula II:

Formula II

10C-AHL is also known as N-(3-oxodecanoyl)-L-homoserine lactone, and has the following Formula III:

Formula III

Also specifically included are 6C-AHL, 8C-AHL, and 14C-AHL. 8C-AHL is also known as N-(3-oxooctanoyl)-L- homoserine lactone, or N-(β-ketooctanoyl)-L-homoserine, and has the following Formula IV:

Formula IV

6C-AHL is also known as N-(β-ketocaproyl)-L-homoserine lactone, or N-(3-oxohexanoyl)-L-homoserine lactone, and has the following Formula V:

Formula V

14C-AHL is also known as N-3-oxo-tetradecanoyl-L-homoserine lactone, or N-3-oxo-myristoyl-L-homoserine lactone, and has the following Formula VI:

Formula VI

Any of the above AHL compounds can be prepared by coupling a carboxylic acid having the general formula $RCOCH_2COOH$, or a salt thereof, with L-homoserine lactone, in the presence of a carbodiimide coupling reagent, where the identity of R determines the identity of the carbon tail of the resulting AHL compound. Other methods of preparing AHL compounds are encompassed within the present disclosure.

Some AHLs are known as quorum sensing molecules produced by several bacterial species, including *Pseudomonas aeruginosa*. Numerous bacterial species are known to communicate through the process called quorum sensing. This communication can take place using a variety of molecules including homoserine lactones, peptides, and even lipids, which act to mediate cell-cell communication between bacterial cells. *Pseudomonas aeruginosa* produces N-oxo-dodecanoyl-L-homoserine lactone (12C-AHL), which is important for communication and virulence of the pathogen. Some AHLs have been shown to affect various activities of eukaryotic cells including fibroblasts, epithelium, and several leukocyte subsets. With regard to immune function, AHLs produced by *P. aeruginosa*, a Gram-negative bacterium that is commonly found to form biofilms in cystic fibrosis lungs, induce mRNA expression of KC and IL-6 while suppressing protein synthesis in mouse fibroblasts. Furthermore, *P. aeruginosa* AHLs have been shown to modulate cytokine secretion both positively and negatively in human macrophage cell lines depending on the stimulus and concentration of AHL. *P. aeruginosa* AHL has also been shown to suppress LPS-induced TNF-α or activation of Iκb using in vivo reporter mice. This activity may take place through activation of PERK (which has been implicated in the ER-stress pathway), NFκB, PPARγ, or other pathways. These uses for AHLs indicate that bacteria have evolved mechanisms by which their intraspecies communication can have effects on interspecies interactions.

Platelets are known for their hemostatic function but are also appreciated for their immune function, especially in combating infectious pathogens. Platelets have been implicated in host defense against infectious agents including *S. aureus, E. coli*, and viruses. The mechanisms by which platelets interact with bacterial pathogens include utilization of plasma proteins such as fibrinogen, IgG, and plasminogen, in addition to the possibility of direct ligation of pattern recognition receptors (Toll-like receptors and scavenger receptors). Platelets have also been shown to have direct bactericidal activities against *E. coli* and *S. aureus*. The mechanism(s) for bacterial killing include platelets surrounding or phagocytosing the bacteria and subsequent release of platelet microbicidal peptides and β-defensins.

Based on the importance of platelets in combating bacterial infections, as well as the knowledge that certain quorum sensing molecules modulate immune function, it was expected that AHLs would activate platelets. However, as described in the examples herein, it has been surprisingly observed that AHLs from *P. aeruginosa* inhibit, instead of activate, select platelet activities by altering intracellular signaling cascades. Specifically, AHLs inhibited the activation of platelets in response to select stimuli and displayed an ability to prevent hypersensitivity of platelets to thrombotic stimuli after exposure to aggregated IgG (aggIgG). Without wishing to be bound by theory, the inhibition of platelet activity appears to be due to suppressed signaling downstream of FcγRIIa. Furthermore, AHLs of longer carbon tail length have been observed to be more potent in their ability to prevent hypersensitivity while maintaining the response to thrombotic stimuli. AHLs appear to have no suppressive effect on the ability of platelets to mediate phagocytosis, which is important for host-defense. Notably, these inhibitors prevent select activities, but response to thrombotic stimuli and host defense activities remain normal. Thus, certain AHLs prevent platelets from clumping together but still allow the platelets to respond normally. Without wishing to be bound by theory, it is believed this is achieved by inhibiting phosphorylations.

Without wishing to be bound by theory, it is believed that the lactone ring of the AHL compounds binds into a kinase, and the tail of the AHL compounds regulates how the molecule fits in the binding site. For instance, if the tail is too short, the molecule is too rigid, and if the tail is too long, the molecule is too flexible; in either case, the molecule would not fit properly in the binding site. Without wishing to be bound by theory, it is believed that a 12-carbon chain is the optimal chain length for inhibiting hypersensitivity of platelets, though AHLs with a 10-carbon chain can also be used very effectively. Though 10C AHL and 12C AHL are described as being optimal, the use of other AHLs to inhibit platelets from becoming hypersensitive and/or to prevent thrombosis, even if not optimal, is encompassed within the present disclosure.

The use of AHLs as described herein provides a solution for pro-thrombotic patients suffering from ailments such as lupus. Lupus patient platelets are hypersensitive to thrombin. However, AHLs prevent platelets from becoming hypersensitive while remaining responsive to thrombotic agents. Furthermore, patients on clopidogrel or other platelet inhibitors for anti-thrombotic therapy are also prone to bleeding. It is now believed that AHLs allow such patients to have normal hemostasis while preventing thrombosis. AHLs avoid excessive bleeding, which is a major complication of other anti-thrombotic drugs.

Pharmaceutical Compositions

Pharmaceutical compositions of the present disclosure comprise an effective amount of an AHL, and/or one or more additional agents such as chemotherapeutic agents, lupus treatments, rheumatoid arthritis treatments, infectious disease treatments, inflammatory disease treatments, or metabolic disease treatments, dissolved or dispersed in a pharmaceutically acceptable carrier. In certain embodiments this can be administered as two independent medications: one for the underlying disease and the second for the prothrombotic state, The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, in utero, orally, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514; 6,613,308; 5,466,468; 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

Furthermore, the compounds and compositions herein can be used in combination therapies. That is, the compounds and compositions can be administered concurrently with, prior to, or subsequent to one or more other desired therapeutic or medical procedures or drugs. In concurrent administration, the two or more therapeutic agents can be administered as part of the same composition, or as two or more compositions. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the AHL can be administered in combination with one or more suitable chemotherapeutic agents, lupus treatments, or rheumatoid arthritis treatments. Suitable chemotherapeutic agents include, but are not limited to: platinum coordination compounds; taxane compounds; topoisomerase I inhibitors, such as camptothecin compounds; topoisomerase II inhibitors, such as anti-tumor podophyllotoxin derivatives; anti-tumor vinca alkaloids; anti-tumor nucleoside derivatives; alkylating agents; anti-tumor anthracycline derivatives; HER2 antibodies; estrogen receptor antagonists or selective estrogen receptor modulators; aromatase inhibitors; differentiating agents, such as retinoids, and retinoic acid metabolism blocking agents (RAMBA); DNA methyl transferase inhibitors; kinase inhibitors; farnesyltransferase inhibitors; HDAC inhibitors; or other inhibitors of the ubiquitin-proteasome pathway. Suitable lupus treatments include, but are not limited to: PI3 kinase inhibitors, corticosteroids, anti-inflammatory agents, immunosuppressants, anti-malarial drugs, statins, and diuretics. Suitable rheumatoid arthritis treatments include, but are not limited to: disease-modifying antirheumatic drugs (DMARDs), anti-inflammatory agents, corticosteroids, and proteins (biologic response modifiers, or biologics).

In some embodiments, the chemotherapeutic agent, lupus treatment, or rheumatoid arthritis treatment is selected from the group consisting of: Belimumab (marketed as Benlysta®), hydroxychloroquine, zathioprine, cyclophosphamide, methotrexate, mycophenolate mofetil, aspirin, ibuprofen, naprosyn, indomethacin, prednisone, prednisolone, sulfasalazine, leflunomide, hydroxychloroquine sulfate, Actemra, Cimzia, Enbrel, Humira, Kineret, Orencia, Remicade, Rituxan, Simponi, etoposide, teniposide, irinotecan, topotecan, vinblastine, vincristine, vinorelbine, 5-fluorouracil, gemcitabine, capecitabine, cisplatin, carboplatin, oxaliplatin, paclitaxel, docetaxel, nitrogen mustard, nitrosourea, cyclophosphamide, chlorambucil, carmustine, lomustine, daunorubicin, doxorubicin, idarubicin, mitoxantrone, trastuzumab, tamoxifen, toremifene, droloxifene, faslodex, raloxifene, exemestane, anastrozole, letrazole, vorozole, accutane, vitamin D, azacytidine, flavoperidol, imatinib mesylate, gefitinib, Velcade®, Yondelis®, oxaliplatin, arabinoside-C, busulfan, irinotecan, and temozolomide.

Kits

It is envisioned that the compounds, compositions, and methods described herein could be embodied as parts of a kit or kits. A non-limiting example of such a kit is a kit for preparing an anti-thrombotic treatment, which includes an AHL compound and a drug delivery instrument, such as a syringe, in separate containers, where the containers may or may not be present in a combined configuration. Many other kits are possible, such as kits comprising an AHL compound and a pharmaceutically acceptable carrier, diluent, or excipient, or kits comprising an AHL compound and a suitable chemotherapeutic agent, lupus treatment, or rheumatoid arthritis treatment for a combination therapy with an AHL. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Examples

Platelet Isolation

Human platelets were isolated from the blood of healthy donors obtained by enipuncture in accordance with the University of Toledo Biomedical IRB and the Declaration of Helsinki. Fresh washed human platelets were prepared as previously described. Briefly, blood was drawn into vacutainers containing 10% ACD solution (BD, Franklin Lakes, N.J., USA): 56 mM sodium citrate, 65 mM citric acid and 100 mM glucose. The blood was centrifuged at 200×g for 10 minutes to obtain platelet rich plasma (PRP). PRP fraction was collected and washed in pH 6.5 buffer containing: 2.75 g/L sodium citrate, 1.0 g/L citric acid, 3.2 g/L glucose, and 8.5 g/L sodium chloride, mixed well and the pH adjusted to 6.5. After washing, platelets were kept in pH 6.5 buffer and stored at room temperature for less than 30 minutes before use. Stimulation took place in a 37° C. water-bath in pH 7.4 buffer containing: 8.0 g/L sodium chloride, 0.2 g/L potassium chloride, 0.2 g/L magnesium chloride, 0.45 g/L sodium phosphate dibasic, 0.9 g/L HEPES, 3.5 g/L bovine serum albumin, 1.0 g/L glucose, and adjusted to pH 7.4.

Platelet Activation

Platelets were incubated for 15 minutes with indicated concentrations of AHL molecules (Sigma Aldrich, St. Louis, Mo.) followed by stimulation with thrombin (Chrono-Log, Havertown, Pa.), or heat-aggregated IgG (aggIgG) prepared as previously described. Briefly, 10 mg/ml of human IgG (MP Biomedicals, Solon, Ohio) was aggregated at 62° C. in PBS for 20 minutes. Insoluble aggregates were removed by centrifugation at 10,000×g for 10 minutes. The soluble fraction of aggIgG-complexes has been characterized as aggregates of 2-6 IgG molecules. Platelets were stimulated with indicated concentrations of thrombin or aggIgG for 30 minutes in a 37° C. water bath. After stimulation, platelets were fixed for 1 hour at 4° C. using 2% paraformaldehyde. Hypersensitivity was assessed by incubating platelets with AHLs as above then exposed to aggIgG for 15 minutes at 37° C. followed by stimulation with thrombin for 30 minutes at 37° C. The platelets were fixed using 2% paraformaldehyde for 1 hour at 4° C. Aliquots of fixed platelets were reacted with APC-conjugated anti-CD42b, and PE-Cy5-conjugated anti-CD62P monoclonal antibodies (B-D Biosciences, San Jose, Calif., USA) or fluorophore and isotype-matched control antibodies for 30 minutes on ice. Platelets were then washed and analyzed by flow cytometry on a FACSCalibur flow cytometer (B-D Biosciences). Platelets were gated on CD42b+ populations and analyzed for CD62P expression. Samples stained with individual fluorophores were used for instrument and compensation settings. Data were analyzed using CellQuest (B-D Biosciences) and FlowJo (Tree Star, Inc., Ashland, Oreg.) software.

Polystyrene Bead Opsonization

Polystyrene beads, 1.5 µm in diameter, (Polysciences, Warrington, Pa.) were opsonized for 2 hours at 21° C. in a 10 mg/ml solution FITC labeled human IgG (SigmaAldrich, St. Louis, Mo.) or unlabeled human IgG for controls. After washing three times in PBS, beads were then resuspended in buffer and counted via hemacytometer.

IgG-Coated Bead Internalization

Platelets in pH 7.4 buffer were exposed to IgG-opsonized beads at a target:effector cell ratio of 10:1. The platelets were allowed to bind IgG-targets on ice for 30 minutes then placed in a 37° C. water bath for 30 minutes to allow for phagocytosis. Following the incubation, aliquots were placed on ice and reacted with APC-conjugated anti-CD42b (B-D Biosciences, San Jose, Calif.) and PE-conjugated anti-human IgG (Rockland Immunochemicals, Gilbertsville, Pa.) for 30 minutes on ice. Platelets were then fixed for 1 hour using 2% paraformaldehyde and washed in PBS.

Samples were prepared for flow cytometry and platelets with associated beads were gated on CD42b+/FITC+ and analyzed for internal/external by the absence/presence of PE expression on a FACSCalibur (B-D Biosciences). Samples reacted with individual fluorophores and isotype matched control antibodies were used for instrument and compensation settings. Data were analyzed using Cell Quest (B-D Biosciences) and FlowJo (Tree Star, Inc., Ashland, Oreg.) software.

Results 10 and 12 Carbon Chain Acyl Homoserine Lactone Derivatives Inhibit Platelet Activation to Select Agents.

Figure 1A:
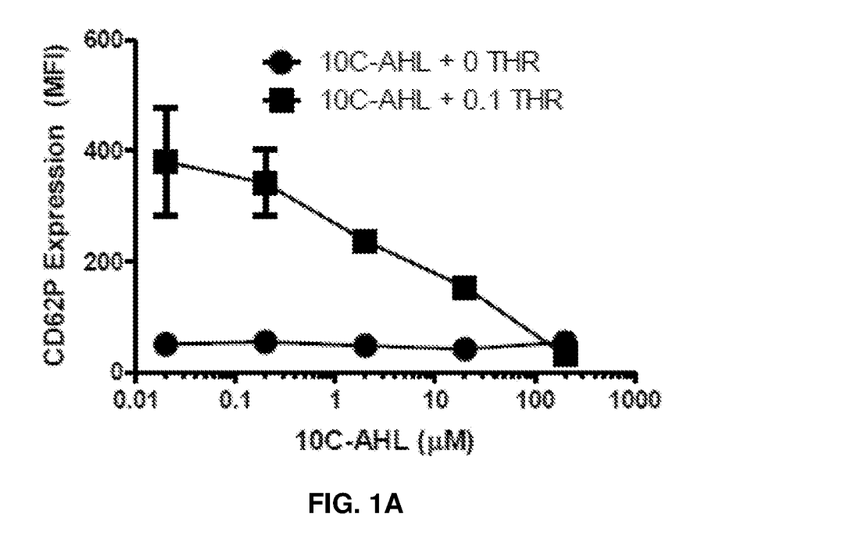
FIGS. 1A-1D: Dose response of AHLs in platelet activation. Platelets were incubated with several doses of 10C- or 12C-AHLs, then stimulated with thrombin (FIGS. 1A-1B) or aggIgG (FIGS. 1C-1D). Exposure of plasma membrane CD62P on CD42b+ platelet populations was measured by flow cytometry.
Figure 1B:
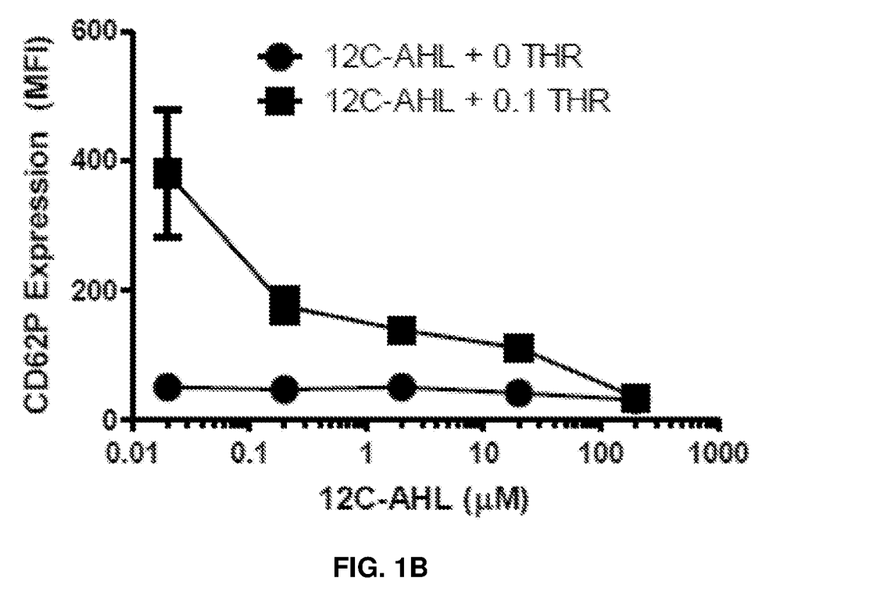
Figure 1C:
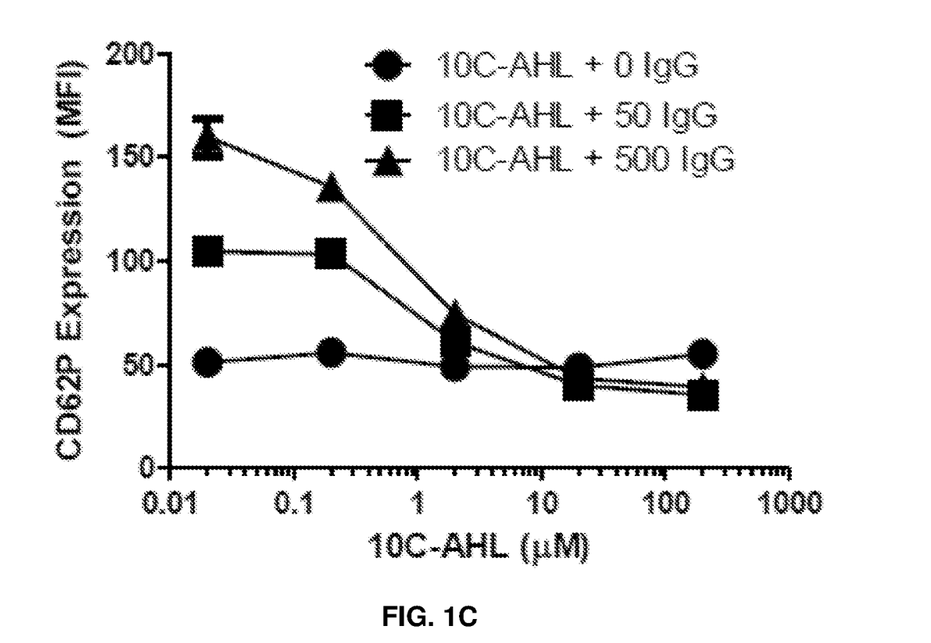
Figure 1D:
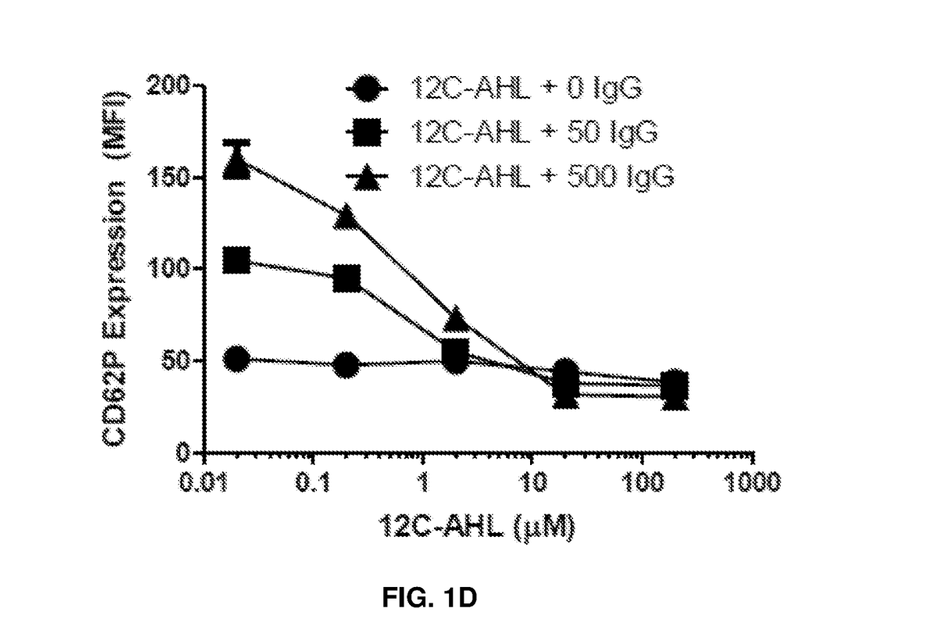

The acyl-homoserine lactone family produced by members of the *Pseudomonas* spp. are common quorum sensing molecules. The ability of two forms of these molecules to inhibit human platelet responses to thrombotic stimuli was tested. To do this, freshly-isolated human platelets were incubated with several concentrations of 10- or 12-carbon AHLs (10C-AHL or 12C-AHL, respectively). FIGS. 1A-1D show platelets incubated with 10C-AHL (FIGS. 1A & 1C) or 12C-AHL (FIGS. 1B & 1D) for 15 minutes at 37° C. then exposed to PBS, 0.1 U/ml thrombin or agglgG (50 or 500 µg/ml) for an additional 15 min at 37° C., which is sufficient to activate platelets. Platelets were fixed using paraformaldehyde and surface expression of P-selectin (CD62P) was detected by flow cytometry as a marker of platelet activation. FIGS. 1A-1D show that 10C-AHL and 12C-AHL inhibit platelet activation by either thrombin or agglgG in a dose-dependent manner. The maximal inhibitory concentration (MIC) for thrombin occurred at 200 µM for both 10C-AHL and 12C-AHL while the MIC for agglgG occurred at <20 µM. At high concentrations, AHLs inhibit platelet activation to thrombotic stimuli. (FIGS. 1A-1B.) At lower concentrations, AHLs inhibit platelet activation to IgG. (FIGS. 1C-1D.)

Altering Carbon Chain Length Affects Inhibitory Activity

Figure 2A:
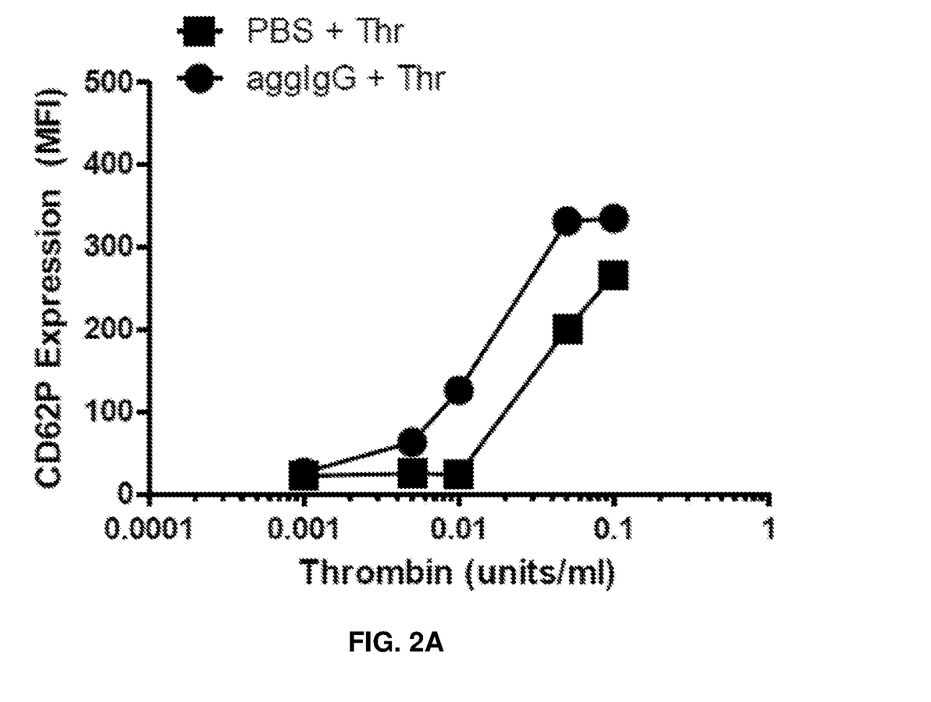
Figure 2B:
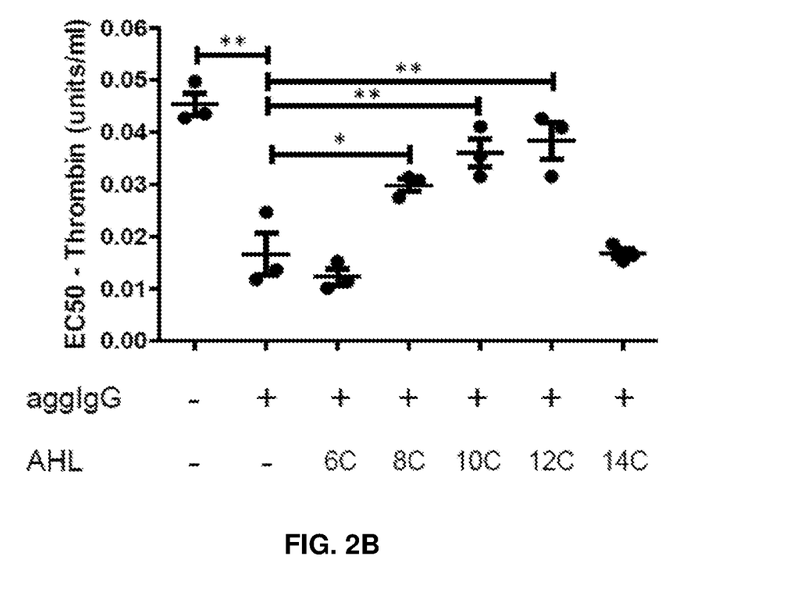

Human platelets become hypersensitive to select thrombotic stimuli after exposure to agglgG (FIGS. 2A-2B). Because low doses of AHLs inhibit agglgG-induced platelet activation compared to thrombin activation, the effect of carbon tail length on inhibition of agglgG-induced hypersensitivity was evaluated. To do this, human platelets were incubated with 20 µM of AHLs with various acyl chain lengths for 15 min at 37° C. followed by stimulation with PBS or agglgG and then a thrombin dose response experiment was performed (FIG. 2B). As seen from FIG. 2B, AHLs block IgG-induced hypersensitivity to thrombin, and the carbon chain length is important. Surprisingly, both 10C-AHL and 12C-AHL return thrombin responsiveness (EC50) values back to those observed in platelets not treated with agglgG. AHLs with shortened carbon tails (6C-AHL) had no effect on platelet activation whatsoever while 8C-AHL partially inhibited the agglgG hypersensitivity. A longer carbon tail AHL (14C-AHL) exhibited no ability to inhibit hypersensitivity. Without wishing to be bound by theory, it is believed that these results indicate the optimal acyl chain length of the AHLs is 10-12C.

Figure 3A:
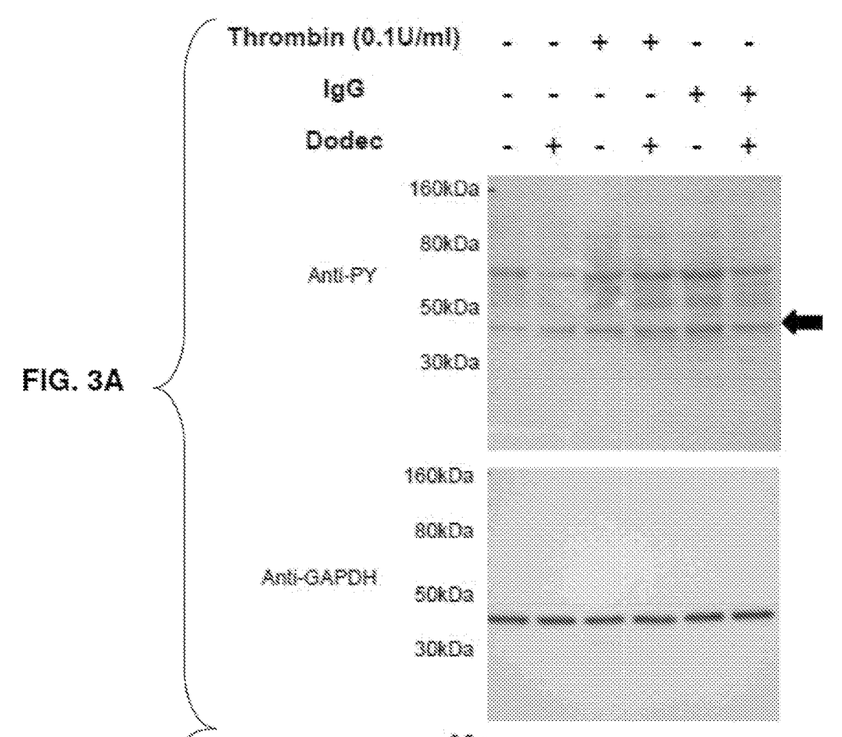
Figure 3B:
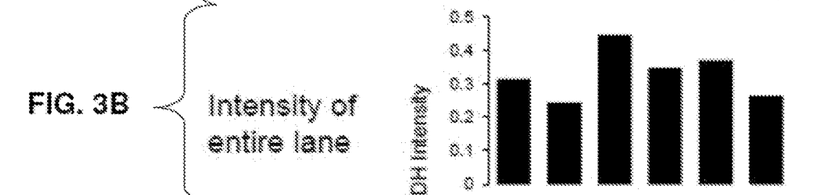
Figure 3C:
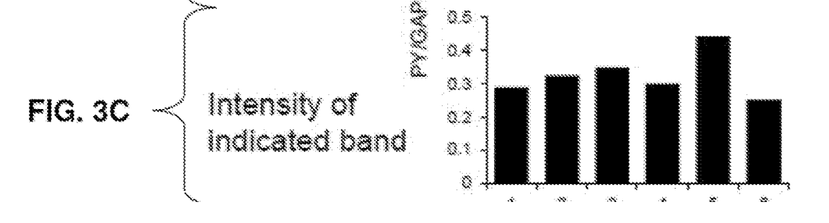

Acyl Homoserine Lactone Derivatives Alter Platelet Tyrosine Phosphorylation Downstream of FcγRIIa Ligation Results from the above experiments indicate that AHLs are altering platelet signaling downstream of FcγRIIa (the receptor for agglgG) and thrombin receptors (PAR1/4) to a lesser extent. To test this, human platelets were incubated with PBS or 20 µM 12C-AHL for 15 min at 37° C. followed by stimulation with thrombin or agglgG. Whole cell lysates were separated by SDS-PAGE and blotted for phosphotyrosine. 12C-AHL had a marginal effect on tyrosine phosphorylation in unstimulated platelets (FIGS. 3A-3C, lane 1 vs. 2) or platelets stimulated with 0.1 U/ml thrombin (FIGS. 3A-3C, lane 3 vs. 4). However, 12C-AHL nearly completely abolished phosphorylation induced by agglgG (FIGS. 3A-3C, lane 5 vs. 6). These results indicate that the AHLs produced by *P. aeruginosa* inhibit signaling activities in platelets, leading to decreased hypersensitivity after agglgG, but do not inhibit the ability of platelets to activate in response to traditional agonists.

AHLs do not Inhibit Host-Defense Activities of Platelets

Figure 4A:
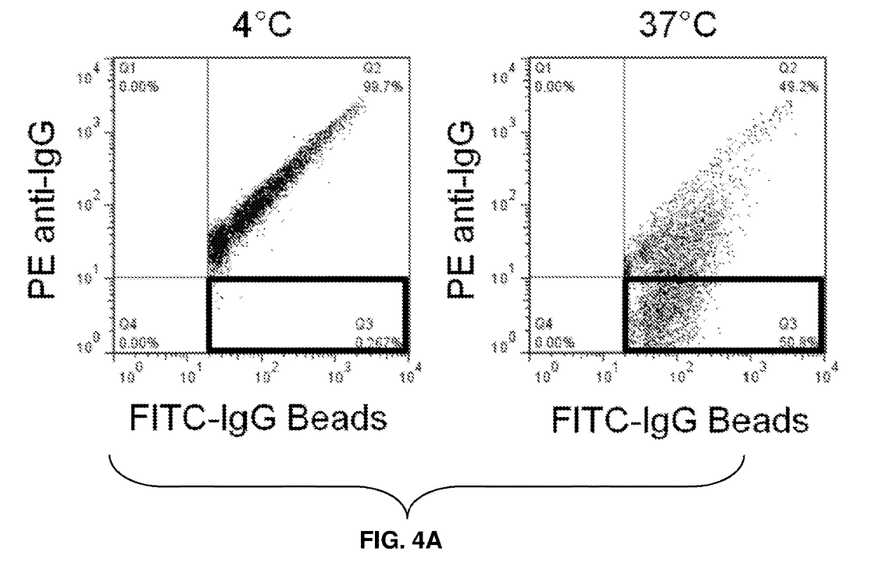
Figure 4B:
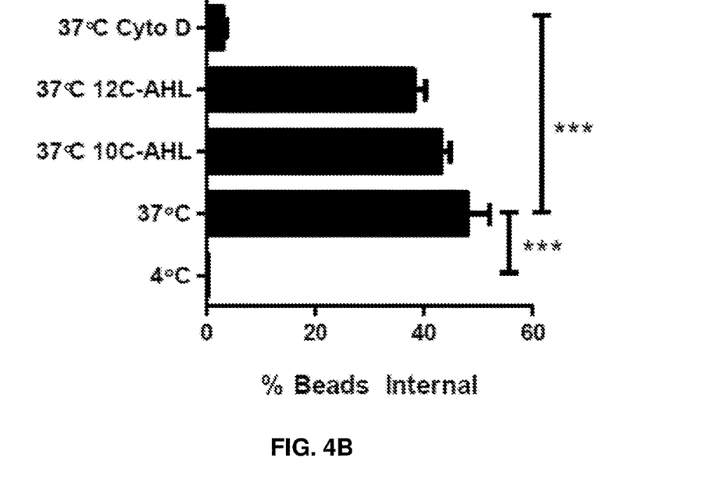
Figure 4C:
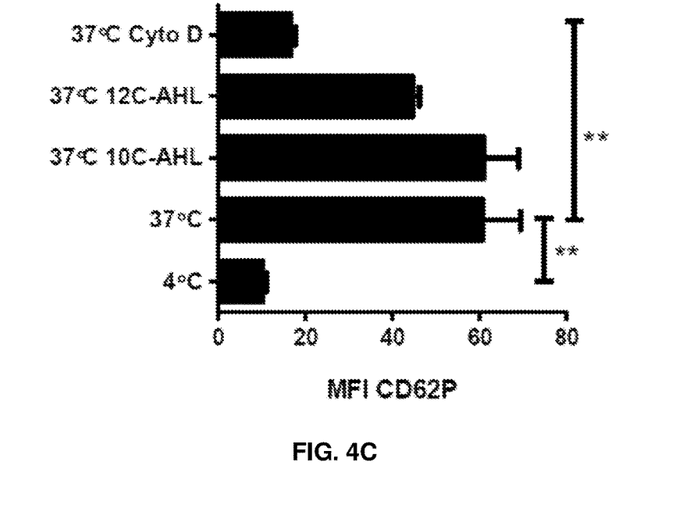

Because AHLs inhibit signaling (especially agglgG-induced tyrosine phosphorylation), whether other platelet activities are inhibited was evaluated. To this end, the affect of AHLs on the ability of platelets to phagocytose IgG-coated latex beads through FcγRIIa was assessed. It was observed that AHLs had no effect on phagocytosis while cytochalasin D inhibited >90% of the phagocytic activity of platelets (FIGS. 4A-4B). Platelet activation (CD62P expression) in response to IgG-coated beads was also not inhibited by AHLs (FIG. 4C), thus maintaining the ability of platelets to adhere to each other, to leukocytes, or to endothelium during the phagocytosis process. All of these activities are essential to maintaining host defense. These results have significant importance for AHLs as therapeutic agents in patients with hypersensitive platelets due to IgG stimulation of FcγRIIa in diseases such as systemic lupus erythematosus, or in patients with anti-phospholipid antibodies.

Figure 5:
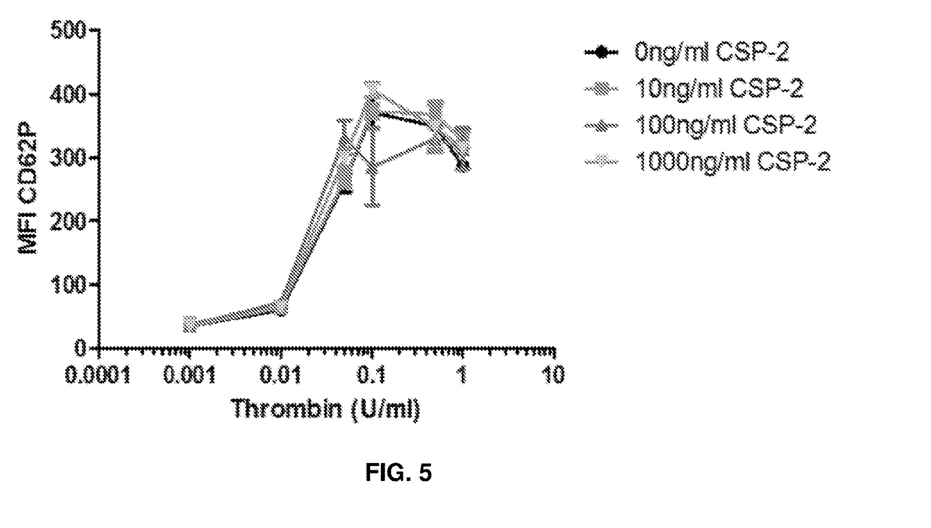
FIG. 5: CSP-1 and CSP-2 do not have any effect on platelet function, and do not act similarly to acyl-homoserine lactone quorum sensing molecules.

Other Quorom Sensing Molecules from *S. pneumonia* do not Exhibit Inhibitor Activities on Human Platelets As described above, certain bacterial communication molecules have a specific inhibitory activity against human platelets. Another communication molecule from *Streptococcus pneumonia*, known as CSP-2, was tested to determine if the inhibitory effect observed from AHLs is conserved across many communication molecules, or if the inhibitory effect is specific to a certain family of molecules. When fresh human platelets were exposed to CSP-2 followed by activation by thrombin, CSP-2 did not display any activity to platelet activities. This is shown in FIG. 5. The same was observed to be true for its related compound CSP-1. Thus, CSP-1 and CSP-2 do not have any effect on platelet function, and do not act similarly to acyl-homoserine lactone quorum sensing molecules.

Discussion

Platelets have been implicated as potent immune cells capable of killing bacteria and controlling bacterial and viral infections. The mechanisms behind these activities are still not understood. Other evidence that platelets are important in the fight against infection include the observation that bacterial species have evolved to produce molecules with dual functionality including communication (quorum sensing) and modulation of platelet activity. AHLs have been shown to manipulate signaling pathways leading to cytokine production in innate immune cells such as macrophages and dendritic cells. Although platelets are anucleate, cytokines and chemokines can be released by pre-formed stores or by inducing translation from pre-existing mRNA after stimulation by platelet agonists.

As shown in FIGS. 1A-1D, AHLs inhibit thrombin activation in a dose-dependent manner. It should be noted that these experiments were performed on platelets stimulated with a sub-maximal dose of thrombin (0.1 U/ml) and platelets stimulated with 1 U/ml of thrombin did not display significant inhibition by any AHLs. Thombin concentrations at sites of clotting will most likely exceed 1 U/ml and therefore will not be inhibited by AHLs thus maintaining the hemostatic ability of platelets. The ability of AHLs to inhibit agglgG-induced hypersensitivity provides for speculation on how *P. aeruginosa* may manipulate platelet function. AgglgG is known to induce platelets to produce significant amounts of sCD40L and RANTES, both of which are known as attractants and activators of immune cells. Without wishing to be bound by theory, one possibility is that at relatively low concentrations (20 nM-2 µM such as those found in cystic fibrosis patient sputum and murine lung infections)

AHLs inhibit platelet activity related to cytokine/chemokine production, while at high concentrations such as those associated with biofilms (reported to reach levels >500 µM), AHLs are able to inhibit all platelet activities including host defense and coagulation. Therefore, low AHLs can prevent leukocyte recruitment to sites of infection while high AHLs can prevent host-defense activities and coagulation that benefits the bacteria.

Certain embodiments of the methods and compositions disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of inhibiting platelets from becoming hypersensitive, the method comprising administering an effective amount of an acyl-homoserine lactone to a patient in need thereof; and inhibiting platelets in the patient from becoming hypersensitive; the acyl-homoserine lactone compound having Formula (I):

Formula I wherein R1 is a carbonyl, and R2 is $(CH_2)_nCH_3$ where n ranges from 4 to 8; and wherein the patient in need has lupus.

2. The method of claim 1, wherein the acyl-homoserine lactone compound consists essentially of 12C-AHL, having Formula II:

Formula II

3. The method of claim 1, wherein the acyl-homoserine lactone compound consists essentially of 10C-AHL, having Formula III:

Formula III

4. The method of claim 1, wherein the acyl-homoserine lactone compound consists essentially of 8C-AHL, having Formula IV:

Formula IV

5. The method of claim 1, wherein the acyl-homoserine lactone compound is administered at an effective concentration, and the acyl-homoserine lactone compound inhibits aggIgG-mediated platelet activation.

6. The method of claim 1, wherein the acyl-homoserine lactone compound is administered at a concentration of about 200 µM or less, and the acyl-homoserine lactone compound inhibits thrombin-induced platelet activation.

7. The method of claim 1, wherein the acyl-homoserine lactone compound inhibits signaling activities in the platelets.

8. The method of claim 1, wherein the patient has a pro-thrombotic condition.

9. The method of claim 1, wherein the acyl-homoserine lactone compound is co-administered with at least one lupus treatment.

10. The method of claim 9, wherein the lupus treatment is selected from the group consisting of: PI3 kinase inhibitors; corticosteroids; anti-inflammatory agents; immunosuppressants; anti-malarial drugs.

* * * * *